(12) United States Patent
Ritter et al.

(10) Patent No.: US 12,048,796 B2
(45) Date of Patent: Jul. 30, 2024

(54) METHOD FOR AUTOMATED PRIMING OF AN EXTRACORPOREAL BLOOD CONDUIT SYSTEM, AND A DEVICE FOR SAME

(71) Applicant: B. Braun Avitum AG, Melsungen (DE)

(72) Inventors: Kai-Uwe Ritter, Melsungen (DE); Sebastian Brögger, Knüllwald (DE)

(73) Assignee: B. Braun Avitum AG, Melsungen (DE)

( * ) Notice: Subject to any disclaimer, the term of this patent is extended or adjusted under 35 U.S.C. 154(b) by 852 days.

(21) Appl. No.: 17/254,896

(22) PCT Filed: Jul. 2, 2019

(86) PCT No.: PCT/EP2019/067684
§ 371 (c)(1),
(2) Date: Dec. 22, 2020

(87) PCT Pub. No.: WO2020/007829
PCT Pub. Date: Jan. 9, 2020

(65) Prior Publication Data
US 2021/0260267 A1 Aug. 26, 2021

(30) Foreign Application Priority Data
Jul. 3, 2018 (DE) ...................... 10 2018 116 071.2

(51) Int. Cl.
*A61M 1/36* (2006.01)
*A61M 60/113* (2021.01)
*A61M 60/279* (2021.01)

(52) U.S. Cl.
CPC ........ *A61M 1/3644* (2014.02); *A61M 60/113* (2021.01); *A61M 60/279* (2021.01)

(58) Field of Classification Search
CPC .............. A61M 1/3644; A61M 1/3643; A61M 1/3647; A61M 60/279; F04B 43/12
See application file for complete search history.

(56) References Cited

U.S. PATENT DOCUMENTS 3,918,854 A * 11/1975 Catarious .......... A61M 5/14232
417/477.11
5,650,071 A 7/1997 Brugger et al.
(Continued)

FOREIGN PATENT DOCUMENTS

DE 102007020573 A1 11/2008
EP 2583701 A1 4/2013
(Continued)

OTHER PUBLICATIONS

Office Action received in Japanese Application No. 2020-573118 dated Jun. 13, 2023, with translation, 21 pages.
(Continued)

*Primary Examiner* — Philip R Wiest
*Assistant Examiner* — Matthew Wrubleski
(74) *Attorney, Agent, or Firm* — Christopher A. Rothe; Culhane PLLC (57) ABSTRACT

A method and apparatus for priming an extracorporeal blood system. The extracorporeal blood system includes an arterial blood line, a venous blood line, a pump segment for interaction with a peristaltic blood pump of the apparatus and a blood treatment unit. A port of the venous blood line is connected to a venous blood port of the blood treatment unit. A port of the arterial blood line is connected to an arterial blood port of the blood treatment unit. The extracorporeal blood system is connected to a reservoir containing priming liquid. The non-occluded extracorporeal blood system is subsequently filled with priming liquid and, after filling with priming liquid, the pump segment is automatically occluded by a blood pump.

8 Claims, 4 Drawing Sheets

(56) References Cited

U.S. PATENT DOCUMENTS

| | | |
|---|---|---|
| 5,776,091 A | 7/1998 | Brugger et al. |
| 6,071,269 A | 6/2000 | Schnell et al. |
| 8,568,115 B2 | 10/2013 | Lauer |
| 2008/0214981 A1 | 9/2008 | Delnevo et al. |
| 2010/0049115 A1 | 2/2010 | Biesel et al. |
| 2012/0103902 A1 | 5/2012 | Childers et al. |
| 2014/0012202 A1 | 1/2014 | Schaefer |
| 2015/0129498 A1 | 5/2015 | Mishima |
| 2015/0367062 A1 | 12/2015 | Brugger et al. |
| 2021/0260267 A1 | 8/2021 | Ritter et al. |

FOREIGN PATENT DOCUMENTS

| | | | |
|---|---|---|---|
| JP | 6075785 A | 4/1985 | |
| JP | 0759845 A | 3/1995 | |
| JP | 2009297193 A | 12/2009 | |
| JP | 2010190062 A | 9/2010 | |
| JP | 2013247971 A | 12/2013 | |
| JP | 2021529056 A | 10/2021 | |
| WO | 9640320 A1 | 12/1996 | |
| WO | 2008077573 A2 | 7/2008 | |

OTHER PUBLICATIONS

International Search Report received in Application No. PCT/EP2019/067684 dated Oct. 8, 2019, 5 pages.

Search Report received in German Application No. 10 2018 116 071.2 dated Feb. 11, 2019, with translation, 20 pages.

Written Opinion received in application No. PCT/EP2019/067684 with translation, dated Oct. 8, 2019, 10 pages.

Third Party Observations Submitted in Japanese Application No. 2020-573118 dated Dec. 20, 2022, with machine translation, 24 pages.

Office Action received in Chinese Application No. 201980044741.0 dated Sep. 17, 2023, with translation, 12 pages.

Office Action received in Chinese Application No. 201980044741.0 dated Feb. 22, 2024, with translation, 12 pages.

\* cited by examiner

METHOD FOR AUTOMATED PRIMING OF AN EXTRACORPOREAL BLOOD CONDUIT SYSTEM, AND A DEVICE FOR SAME

CROSS-REFERENCE TO RELATED APPLICATIONS

This application is the United States national stage entry of International Application No. PCT/EP2019/067684, filed Jul. 2, 2019, which claims the benefit of priority of German Application No. 10 2018 116 071.2, filed Jul. 3, 2018. The contents of International Application No. PCT/EP2019/067684 and German Application No. 10 2018 116 071.2 are incorporated by reference herein in their entireties.

FIELD

The invention relates to a method of priming an extracorporeal blood system for treatment by means of an apparatus for extracorporeal blood treatment, wherein the extracorporeal blood system comprises an arterial blood line, a venous blood line, a pump segment for interaction with a blood pump, especially a peristaltic blood pump, of the apparatus and a blood treatment unit, especially a dialyzer.

In addition, the invention relates to an apparatus for extracorporeal blood treatment comprising a blood pump for delivering liquid in a pump segment, especially a peristaltic blood pump for delivering liquid by peristaltic deformation of a pump segment, of an extracorporeal blood system including an arterial blood line, a venous blood line, the pump segment and a blood treatment unit, especially a dialyzer, wherein the blood pump includes a partially circular guiding surface and a rotor being rotationally driven about a substantially horizontal axis of rotation and interacting with the guiding surface such that in the pump segment arranged between the guiding surface and the rotor a cross-sectional constriction is formed, the apparatus being especially suited for carrying out the method according to the invention.

BACKGROUND

Prior to extracorporeal blood treatment such as a dialysis, air has to be removed from the so-called extracorporeal blood system, substantially consisting of blood tubes (set of blood tubes) and a dialyzer. This is done by displacing and removing as completely as possible air present in the system by introducing a liquid (priming liquid). This operation is generally referred to as priming.

As a priming liquid either sterile saline solution from a bag or, in so-called online machines having two dialysis fluid filters, ultra-pure dialysis fluid from the machine is used. The requirements to the purity of the priming liquid are very high, as impurities and lacking sterility of the system have to be avoided, as is understood, and the priming volume is usually bolus-infused to the patient's blood circulation. For the same reason, no or only very little air should be present in the priming liquid.

For priming an extracorporeal blood system, there are different methods known in the state of the art. In a known method which is also referred to as manual priming or single-pass method, the arterial and venous blood lines of the extracorporeal blood system are initially connected to the blood treatment apparatus (dialysis machine) in the way defined for the treatment. This means that at least one of the lines is inserted into a blood pump of the apparatus and is occluded, i.e. is squeezed in a way required for delivering liquid through the pump. In a number of steps to be carried out manually, the arterial blood line, the venous blood line and the dialyzer then are filled with priming liquid, the priming liquid being guided into and through the extracorporeal blood system by means of a pumping action of the pump.

In a similar method which is also referred to as manual gravity priming, the blood line is initially not occluded by the pump and the priming liquid is introduced to the system by the effect of gravity until the pump segment of the blood line is filled with priming liquid. For example, the pump segment of the tube not filled with liquid may be suspended in the pump in a non-occluding manner. The pump in this case serves merely as a holder and the pump segment could also be suspended at a different position, for example at an IV pole or the like. One end of an arterial tube line pinched off by a clamp is connected to a saline solution bag for filling. The opposite end of the tube line is held up so as to prevent priming liquid, in this case saline solution, from draining. Then the clamp is opened and saline solution flows out of the bag into the tube segment to be primed. Only after the pump segment has been filled free from air, is it threaded into the blood pump and is occluded. By a number of steps to be carried out manually, then the priming liquid is guided into and through the extracorporeal blood system by means of a pumping action of the blood pump. For this purpose, the filled arterial tube segment is connected to the blood side of the dialyzer. Then the venous tube segment is connected to the dialyzer and the dialyzer is filled from the arterial connection/port while the blood pump is running. When the entire blood line and the dialyzer are completely filled with priming liquid, the patient-side connections/ports of the blood line are interconnected. The blood pump is started and the priming liquid is circulated in the extracorporeal system. In the next step, the dialyzer is filled with dialysis fluid via its dialysis fluid ports. In the following, the levels of the priming liquid can be set in the arterial tube line and in the venous tube line by draining air from a drip chamber e.g. via service lines. The extracorporeal blood system now is completely filled with priming liquid which is circulated in the same until the patient arrives and the actual treatment starts.

From WO 2008/077 573 A2 a method of priming a set of blood tubes including a venous line and an arterial line is known, the patient-side ports of which communicate with two separate inlets of a compartment, especially a bag, and the machine-side ports of which communicate with a dialyzer. The method comprises the steps of a parallel filling of both the venous and the arterial lines via a feed line so that priming liquid flows through both inlets into the compartment, as well as of circulating the priming liquid in the circuit consisting of the lines, the dialyzer and the compartment via a pump so that one of the inlets of the compartment acts as an inlet and the other acts as an outlet.

From WO 1996/040 320 A1 a method of prefilling a dialysis machine is known including a dialyzer, a pump and a set of blood tubes which comprises an arterial line for sucking blood from a patient, a pump head for the pump for pumping the blood to the dialyzer, a venous line for returning the blood pumped through the dialyzer to the patient and a connector for connecting the arterial line and the venous line, the method comprising the following steps of:
  connecting the arterial line and the venous line to the connector;
  connecting the connector to a drain line;
  interconnecting a drain valve between the connector and the drain line;
  filling the arterial line with a sterile solution;

opening the drain valve and an arterial clamp at the arterial line so that the sterile solution in the arterial line flows through the connector and flows past the open drain valve downwards in the drain line;

closing the arterial clamp;

opening a venous clamp at the venous line and operating the pump in a forward direction to suck sterile solution from the arterial line through the pump head and the dialyzer and to enable the sterile solution to flow through the venous line and the connector past the open drain valve downwards in the drain line; and closing the drain valve, opening the arterial clamp and operating the pump to return the sterile solution through the dialyzer and the set of blood tubes.

It is a substantial drawback of known priming methods that usually a certain amount of air remains enclosed in the extracorporeal line system which has to be removed in the course of priming e.g. by knocking, shaking or similar manual activities to be thoroughly carried out by the operating staff. Although gravity priming constitutes an especially proper possibility of removing air almost completely from the extracorporeal blood system. However, it cannot be automated at present, since in automatic priming the pump segment of the blood line is inserted already into the blood pump during set-up and in known machines having an automatic threading function the pump segment is inserted and automatically threaded into the pump as soon as the cover of the pump is closed.

It is a drawback in methods applying no gravity priming that after filling of the system the arterial line and the venous line are connected and then the priming liquid is circulated so as to remove leftover air bubbles. The latter accumulate in the air separator and lower the level there, thus rendering an additional operating step necessary because the level has to be newly set in the air separator.

Another drawback in known automated methods may be leftover air which remains in the pump segment and is chopped or foamed into micro-bubbles by the pumping action of the pump. Said micro-bubbles are undesired as, under certain circumstances, they may result in microembolisms in the patient. Moreover, additional microbubbles may trigger undesired alarm. Finally, in known automatic methods it is not possible due to the occlusion of the blood tube to compare and adapt pressure sensors upstream and downstream of the pump to each other as part of preparing the machine for treatment.

SUMMARY

On the basis of the above-described state of the art, the object underlying the invention is to eliminate the above-listed drawbacks, especially to improve and to at least partially automate the preparation process of extracorporeal blood treatment, especially of dialysis, as well as to provide an apparatus which is particularly suited for carrying out the method according to the invention.

According to the invention, this object is achieved by a method of priming an extracorporeal blood system for a treatment by means of an apparatus for extracorporeal blood treatment, with the extracorporeal blood system comprising an arterial blood line, a venous blood line, a pump segment for interaction with a blood pump of the apparatus and a blood treatment unit, especially a dialyzer, wherein a port of the venous blood line is connected to a venous blood port of the blood treatment unit, a port of the arterial blood line is connected to an arterial blood port of the blood treatment unit and the extracorporeal blood system is connected to a reservoir containing priming liquid, after than the non-occluded extracorporeal blood system is filled with priming liquid and the pump segment is automatically occluded, after filling with priming liquid, by means of a blood pump of the blood treatment apparatus. It can also be stated that the extracorporeal blood system is filled with priming liquid in a non-occluded state and the pump segment is automatically occluded by the blood pump after filling with priming liquid.

This object is further achieved by an apparatus for extracorporeal blood treatment comprising a blood pump for delivering liquid in a pump segment, especially a peristaltic blood pump for delivering liquid by peristaltic deformation of a pump segment, of an extracorporeal blood system comprising an arterial blood line, a venous blood line, the pump segment and a blood treatment unit, especially a dialyzer, the blood pump including a partially circumferential guiding surface and a rotor rotationally driven about a substantially horizontal axis of rotation which interacts with the guiding surface such that in the pump segment arranged between the guiding surface and the rotor a cross-sectional constriction is formed, wherein the guiding surface extends from an area beneath the rotor partially around the latter to an area above the rotor and is open towards the side. The term "open towards the side" has to be understood with respect to the field of gravity of the earth, wherein the term "beneath" denotes directed toward the earth, the term "above" denotes facing away from the earth and the term "toward the side" denotes the areas between the "above" and the "beneath". Due to this orientation of the guiding surface of the blood pump relative to the field of gravity of the earth, the pump segment can be advantageously arranged in the pump in such a way that it is mandatorily filled from "the bottom" to the "top" with priming liquid so that filling and priming may take place especially easily and efficiently free from air. Open toward the side in this context means that the guiding surface surrounds the rotor axis over a wrapping angle area, for example from about 260° to 280°, preferably 270°, and the remaining area of from about 80° to 100°, preferably 90°, is open, with said remaining area being arranged laterally next to the rotor axis with respect to the horizontal line and the field of gravity of the earth.

The blood pump may especially be a peristaltic pump. It may include a pump housing having a partially circular guiding surface within which a rotor is arranged to be rotationally driven so as to squeeze a tube line provided between the guide surface and the rotor for delivering liquid. The apparatus and/or the blood pump may further include a retaining contour for retaining the blood line(s) in a non-closing/non-occluding manner. Preferably, the blood pump is arranged in or at a substantially vertical machine front side of the apparatus for extracorporeal blood treatment.

The arterial blood line, the venous blood line and the pump segment may be formed, within the scope of the invention, as especially elastically deformable fluid lines or tubes.

It can also be stated that, according to the invention, the extracorporeal blood system initially is completely set up and disposed at the apparatus for extracorporeal blood treatment. It may even be connected to the apparatus in the manner determined for treatment with the exception that the pump segment is not occluded. Not occluded in accordance with the invention means that the priming liquid may flow, in particular unhindered, through the pump segment. For example, this can be achieved by preventing the pump segment from being squeezed by the blood pump.

One embodiment of the apparatus is characterized in that the extracorporeal blood system is connected to a reservoir containing priming liquid by connecting a patient-side port of the venous blood line or a patient-side port of the arterial blood line or a filling line fluid-connected thereto to the reservoir containing priming liquid. In this way, the blood system per se can be completely set up, i.e. especially the arterial blood line, the venous blood line and the treatment device can be interconnected as intended so that for priming and subsequent treatment advantageously only very few steps have to be taken.

According to another embodiment, the patient-side port of the venous blood line is connected to the reservoir containing priming liquid and subsequently the extracorporeal blood system is filled from the arterial side to the venous side, with the reservoir being especially a substitute port of the apparatus or an external reservoir containing priming liquid. Filling from the arterial side to the venous side in this context means that the priming liquid is fed to the arterial blood line and from there flows to the venous blood line through the blood system. For better removal of air from the system and from the priming liquid, in the further course of priming the direction of flow of the priming liquid in the blood system may be reversed once or several times.

One embodiment of the invention is characterized in that the patient-side port of the arterial blood line is connected to the reservoir containing priming liquid and subsequently the extracorporeal blood system is filled from the venous side to the arterial side, with the reservoir being especially a substitute port of the apparatus or an external reservoir containing priming liquid. Filling from the venous side to the arterial side in this context means that the priming liquid is fed to the venous blood line and from there flows to the arterial blood line through the blood system This is opposite to the direction which is typically used for priming. By priming from the venous side to the arterial side, air can be completely displaced from a venous air trap usually provided in the apparatus for blood treatment, as the latter then is filled from the bottom. This is especially beneficial to so-called air-free blood lines. For better removal of air from the system and from the priming liquid, in the further course of priming the direction of flow of the priming liquid in the blood system can be reversed once or several times.

In accordance with another embodiment of the invention, prior to filling with priming liquid a patient-side port of the venous blood line or a patient-side port of the arterial blood line (i.e. a port which is not connected to the reservoir containing priming liquid) may be connected to a process liquid port (waste port) of the apparatus for extracorporeal blood treatment or to a separate process liquid reservoir, especially to a waste container or waste bag. Connected in this context means connected in a fluidically and preferably non-contacting manner. In this way, excess priming liquid can be disposed of especially easily and hygienically.

In another embodiment of the invention, the pump segment can be inserted into or positioned relative to the blood pump prior to filling with priming liquid so that during the filling of priming liquid into the blood system it is not occluded by the blood pump (and preferably will not be occluded during the filling of priming liquid, either) and is occluded (only) after the extracorporeal blood system has been filled completely with priming liquid. Especially, the pump segment can be introduced to and occluded in the delivering path of the blood pump automatically by activating the same. For this purpose, the apparatus according to the invention and/or the blood pump thereof may include at least one retaining device to retain the pump segment to be non-occluding in a manner enabling automatic threading of the pump segment into the blood pump.

Alternatively, the pump segment can be inserted into a delivering path of the blood pump prior to the filling with priming liquid, with the blood pump being configured so that the pump segment is not and will not be occluded by the blood pump during the filling of the extracorporeal blood system with priming liquid and the pump segment is occluded in the delivering path after complete filling of the extracorporeal blood system with priming liquid. This may be achieved, for example, by the blood pump as a peristaltic blood pump being provided with a rotor adapted to be positioned relative to the guiding surface and/or with pressing rolls adapted to be positioned relative to the guiding surface which, during priming and, resp., filling the blood system with priming liquid, is/are in a position not occluding the pump segment and for delivering priming liquid can be positioned in a position relative to the guiding surface occluding the pump segment. As regards the apparatus according to the invention it is noted that the rotor of the blood pump may be adapted to be positioned and/or tilted especially relative to the guiding surface in a direction transversely to its axis of rotation and/or may include pressing elements adapted to be positioned relative to the axis of rotation of the rotor in the radial direction. According to one embodiment, the rotor of the pump can be positioned together with a guide element for guiding the pump segment in a non-occluding position relative to the guiding surface. The guide element may be disposed especially above the rotor and thus also above the pump segment.

According to the invention, the blood pump may be operated during priming in a delivering direction opposed to the delivering direction during blood treatment. In this way, filling of the blood system with priming liquid and/or priming liquid flowing through the blood system from the venous side to the arterial side can be achieved in an especially simple manner without conversion of the blood system at the machine being necessary.

According to one embodiment of the method according to the invention, the blood system is connected to the apparatus for extracorporeal blood treatment prior to filling with priming liquid in a manner determined for treatment, with the exception that the pump segment is not occluded. This means that the apparatus is set up with the blood system in such a way that for carrying out treatment merely the pump segment has to be occluded. In this way, a particularly efficient possibility of preparing extracorporeal blood treatments is provided.

Within the scope of the invention, especially prior to filling the extracorporeal blood system with priming liquid a sensor test run can be carried out. This can take place especially by closing the arterial blood line and the venous blood line in an especially simple manner by means of tube clamps and by increasing the pressure, in particular the air pressure, in the extracorporeal blood system. Moreover, within the scope of the invention, pressure sensors can be repeatedly tested after priming and even during treatment by comparing and checking measuring values of the pressure sensors when the pump segment is not occluded. For this purpose, merely the pump segment has to be transferred from the occluded state to the non-occluded state. This can be carried out automatically or manually by an operating person. In an advanced design of the apparatus suited for automatic transfer to the non-occluded state, the pump is configured so that the pump segment at any time can be removed from the delivering path in an automated manner and, after completed pressure measurement, can be placed in the delivering path in an automated manner again. Alternatively, this can be performed by an above-described positioning of pressing elements of the rotor and/or of the rotor relative to the guiding surface. In this way, it is especially easy to carry out sensor testing as part of treatment by un-threading/un-occluding the pump segment, comparing and, were necessary, correcting/calibrating the pressure and then re-threading/occluding the pump segment again and continuing the treatment.

Basically, according to the invention, the priming liquid can be filled into the extracorporeal blood system by means of excess pressure from a substitute port of the apparatus or by means of hydrostatic pressure.

Summing up, it can be stated that especially the following advantages and improvements can be achieved by the invention:

- particularly easy handling by few steps to be carried out by operating staff
- highly flexible with the option to fill from the venous side to the arterial side and vice versa
- improved air removal during priming
- far-reaching automation possible
- adaptation of venous and arterial pressure sensors during priming can be enabled and backed
- as compared to filling of the blood system according to the state of the art (from the arterial side to venous side), a working step of setting a level in the dripping chamber can be dispensed with by venting the chamber

BRIEF DESCRIPTION OF THE DRAWING FIGURES

Hereinafter, the invention shall be described in detail by way of exemplary non-limiting embodiments shown in the enclosed Figures, wherein.

DETAILED DESCRIPTION

Figure 1:
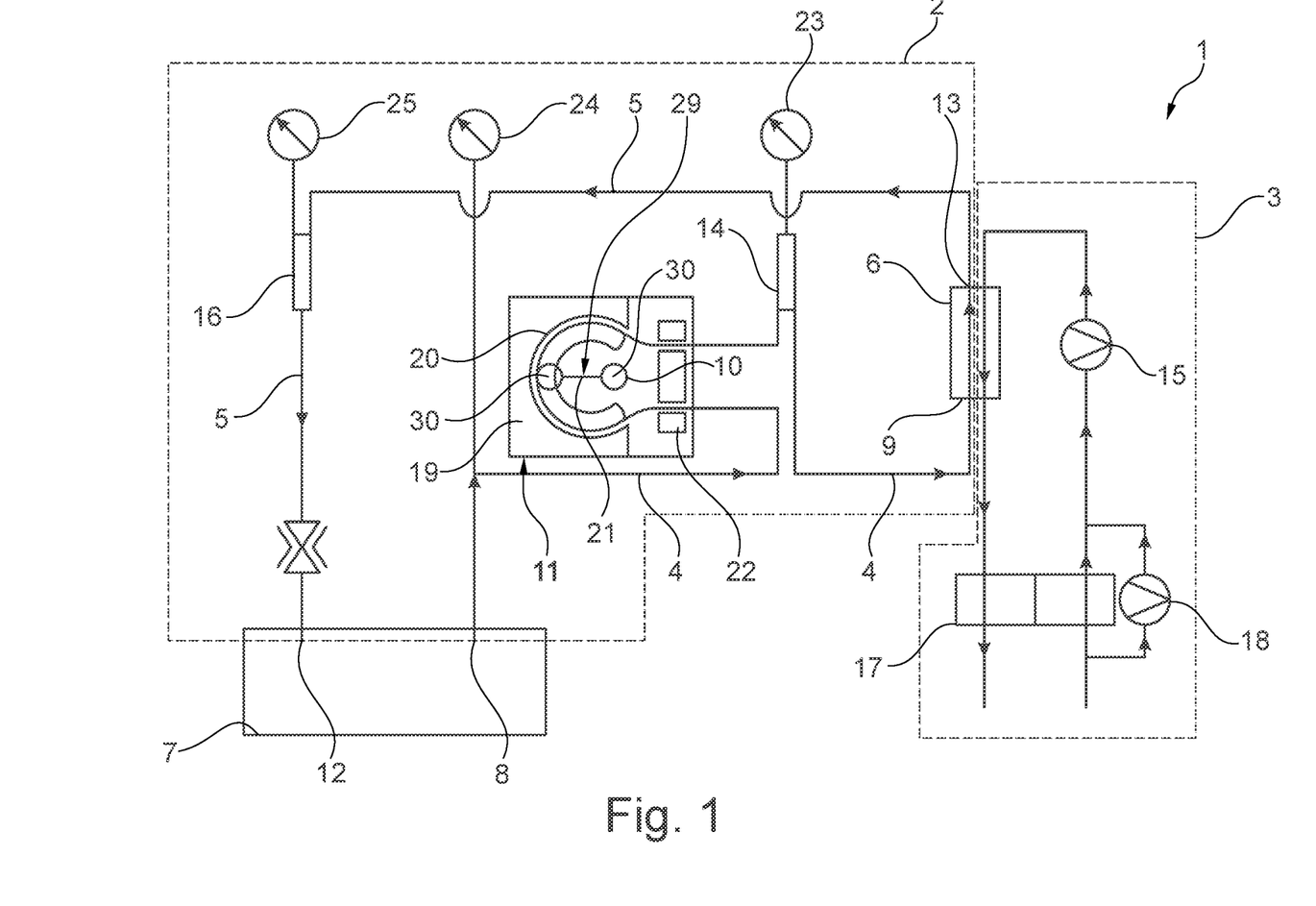
FIG. 1 shows a schematic circuit diagram of an apparatus for extracorporeal blood treatment during blood treatment.

FIG. 1 illustrates in a schematic circuit diagram the liquid system 1 of an apparatus for extracorporeal blood treatment, here in the form of a dialysis apparatus, during treatment such as hemodialysis, hemofiltration or hemodiafiltration. The liquid system comprises an extracorporeal blood system 2, also referred to as extracorporeal blood circuit, and a dialysis fluid circuit 3.

The extracorporeal blood system 2 substantially consists of an arterial blood line 4, in this case in the form of an arterial tube line 4, a venous blood line 5, in this case in the form of a venous tube line 5, and a blood treatment unit 6 in the form of a filter 6 or a dialyzer 6. During blood treatment, the extracorporeal blood system 2 connects a patient 7 indicated in FIG. 1 to the dialysis apparatus.

The arterial blood line 4 includes a patient-side port 8 in the form of an arterial cannula 8 as well as a filter-side port 9 in the form of a Luer connector 9. Moreover, the arterial blood line 4 comprises a pump segment 10 for interaction with a blood pump 11 of the blood treatment apparatus. The venous blood line 5 comprises a patient-side port 12 in the form of a venous cannula 12 as well as a filter-side port 13 in the form of a Luer connector 13. By way of flow direction arrows it is indicated in FIG. 1 that blood is taken from the patient 7 during treatment by means of the arterial cannula 8 and is delivered by means of the blood pump 11 through the arterial blood line 4 via an arterial air trap 14 to the dialyzer 6. In the latter, the actual treatment, purification in this case, of the blood takes place. From the dialyzer 6 the blood flows through the venous blood line 5 and a venous air trap 16 to the venous cannula 12 back into the patient 7. The dialyzer 6 is also integrated in the dialysis fluid circuit 3 and dialysis fluid which is delivered by means of a dialysis fluid pump 15 flows through the dialyzer in a counterflow. The dialysis fluid circuit 3 moreover includes a balancing unit 17 and an ultra-filtration pump 18.

The blood pump 11 is in the form of a peristaltic pump 11. It includes a pump housing 19 having a partially circular guiding surface 20, a rotor 21 including pressing elements 30, e.g. in the form of pressing rolls 30, which is rotatably driven about a substantially horizontal rotor axis or axis of rotation 29 within the partially circular guiding surface 20 as well as a retaining contour 22 for retaining the arterial blood line 4 in a non-closing/non-occluding manner. As is evident from the Figures, the pump segment 10 is part of the arterial blood line 4, viz. the part located between the guiding surface 20 and the rotor 21 in the blood pump 11. Within the scope of the invention, the pump segment 10 may further be configured as a separate elastically deformable fluid line which is connected to the arterial blood line 4 on both sides. During blood treatment, the pump segment 10 is deformed and squeezed, i.e. occluded, by the action of the rotor 21 between the latter and the guiding surface 20 of the pump housing 19 in such a way that fluid is conveyed from the low-pressure side of the arterial blood line 4 to the high-pressure side thereof (indicated by flow direction arrows in FIG. 1).

Figure 2:
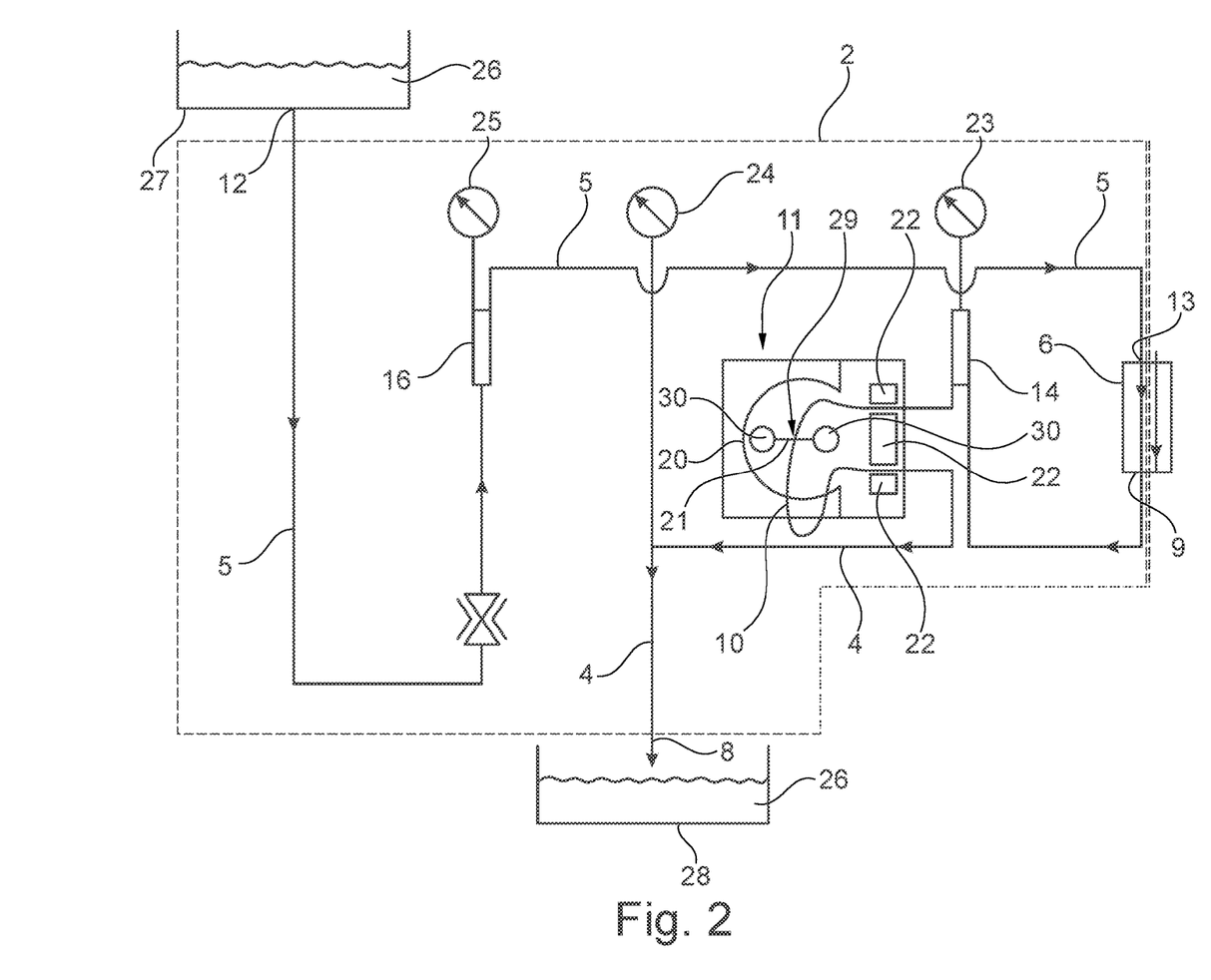
FIG. 2 shows a schematic circuit diagram of the apparatus for extracorporeal blood treatment of FIG. 1 during a first sequence of preparing the blood treatment (priming)
Figure 3:
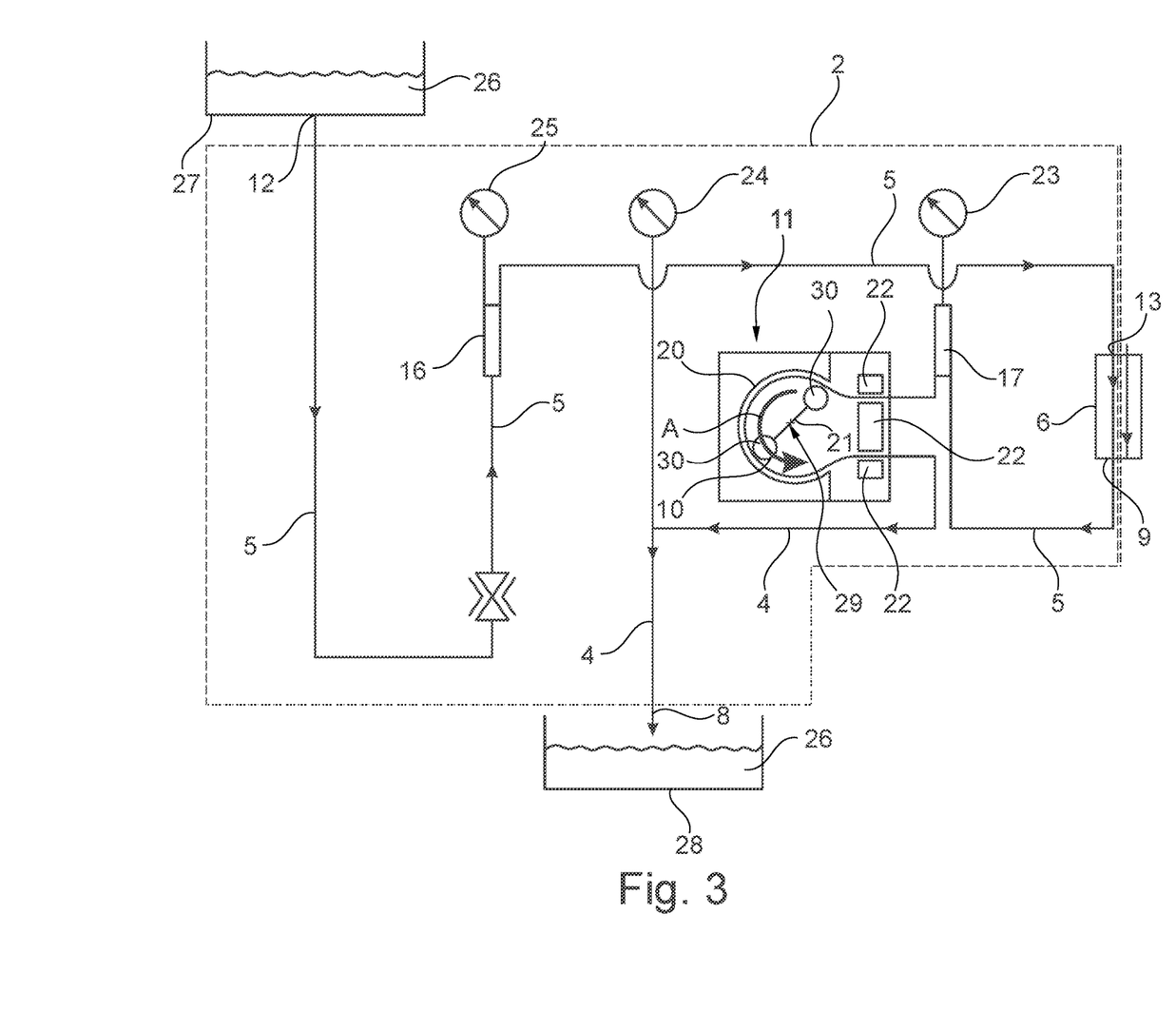
FIG. 3 shows a schematic circuit diagram of the apparatus for extracorporeal blood treatment of FIG. 1 during a second sequence of preparing the blood treatment (priming)

The apparatus for extracorporeal blood treatment shown in FIGS. 1, 2 and 3 moreover may comprise further measuring units, pumps, bubble traps etc. which are not shown. For monitoring therapeutic operations, it includes especially pressure transducers or pressure sensors 23, 24, 25. In detail, these are an inlet pressure sensor 23 sensing the pressure on the high-pressure side of the blood pump 11, an arterial pressure sensor 24 between the arterial cannula 8 and the blood pump 11 as well as a venous pressure sensor 25 in the area of the venous air trap 16.

FIG. 2 illustrates the liquid system 1 shown during treatment in FIG. 1 during a first sequence of priming/the preparation for the treatment as part of a method according to the invention. FIG. 3 illustrates the liquid system 1 during a second sequence of priming/the preparation for treatment following the first sequence as part of a method according to the invention. Other than during treatment, during the preparation the arterial patient-side port 8 and the venous patient-side port 12 are not connected to the bloodstream of a patient. Rather, the arterial patient-side port 8 is connected to a liquid reservoir 27 containing priming liquid 26 and the venous patient-side port 12 is connected to a process liquid reservoir 28. The liquid reservoir 27 may especially be an internal reservoir 27 of the apparatus for extracorporeal blood treatment having a substitute port or an external reservoir 27 containing priming liquid. The process liquid reservoir 28 may especially be an internal process liquid reservoir 28 having a process liquid port (waste port) of the apparatus for extracorporeal blood treatment or a separate process liquid reservoir 28, especially a waste container or waste bag.

It is a special feature of the method according to the invention shown in detail in FIG. 2 that during preparation/priming the pump segments 10 is not and will not be occluded by the blood pump 11. In the method according to the invention, initially the extracorporeal blood system 2 is completely set up. This means that initially the filter-side port 13 of the venous blood line 5 as well as the filter-side port 9 of the arterial blood line 4 are connected to the blood treatment unit (filter, dialyzer). After that, the patient-side arterial port 8 is connected to the process liquid reservoir 28 and the patient-side venous port 12 is connected to the liquid reservoir 27. Alternatively, the patient-side ports 8 and, resp., 12 can be connected to the substitute port and, resp., the waste port of the machine for automatic priming. In the present case, the liquid reservoir 27 is a simple container 27 containing saline solution as priming liquid 26. The blood system 2 is not yet filled with liquid.

The pump segment 10 not filled with liquid is inserted into the retaining contour 22 of the blood pump 11 and is not occluded by the pump. As an alternative, the pump segment 10 may be suspended over the rotor 21 of the blood pump 11 such that it is held at the rotor 21 but is not squeezed or occluded between the rotor 21 and the guiding surface 20. According to another alternative, it may simply be suspended over a hook or an IV pole not shown in the Figures. What is essential is that no occlusion takes place, viz. that the cross-section of the blood line is not closed. In this way, the pump segment 10 is continuously open during the filling operation of the blood system 2 with priming liquid 26.

In the following, the blood system 2 is completely filled with priming liquid 26. Filling is carried out, for example, by means of excess pressure from the substitute port (preferably by means of a substitute pump or any other pump of the apparatus) or by means of hydrostatic pressure from the saline solution reservoir 27. Only when the blood system 2 is completely filled, i.e. the arterial blood line 4, the venous blood line 5, the pump segment 10 and the treatment unit 6, the pump segment 10 optionally can be automatically threaded. This may be simply carried out by activating the blood pump 10, which allows the rotor 21 to automatically seize the line retained in the retaining contour 22 and to place and occlude the same in the manner intended for delivering liquid between itself and the guiding surface. In the further course of priming, the priming liquid 26 is delivered through the blood system 2 from the venous side to the arterial side e.g. by a reverse rotation of the blood pump 10; this direction of rotation is marked by arrow A in FIG. 3.

In the fluid-connection of the blood system 2 to the liquid reservoir 27 and to the process liquid reservoir 28 and, resp., the apparatus for extracorporeal blood treatment as illustrated in FIGS. 2 and 3, in the first sequence of preparation, especially when filling the blood system with priming liquid, priming takes place from the venous side to the arterial side, as is indicated by the flow direction arrows included in FIGS. 2 and 3. This is opposite to the direction typically used for priming. By priming from the venous side to the arterial side air can be completely displaced from the venous air trap 16 as the latter is filled from the bottom. This is of particular advantage for so-called "air-free blood lines". It is pointed at the fact that, within the scope of the method according to the invention, in the second sequence of preparation, especially after the blood system has been filled with priming liquid, the priming liquid can be delivered in both flow directions through the system, even if in FIG. 3 flow arrows point in one direction only.

A method step which is not mandatory consists in carrying out a test of the sensors 23, 24, 25 prior to actually filling the blood system with priming liquid. To this end, the arterial blood line 4 and the venous blood line 5 can be closed by means of arterial and venous stop clamps not shown in the Figures. By means of a pump integrated in the machine, for example, then the air pressure in the blood system can be increased by inflow via a pressure port. Since all sensors 23, 24, 25 are hydraulically interconnected via the non-occluded lines of the extracorporeal blood system 2, they can be tested relative to each other. A possible offset due to a hydrostatic difference in pressure resulting from the height difference has to be taken into account.

Figure 4:
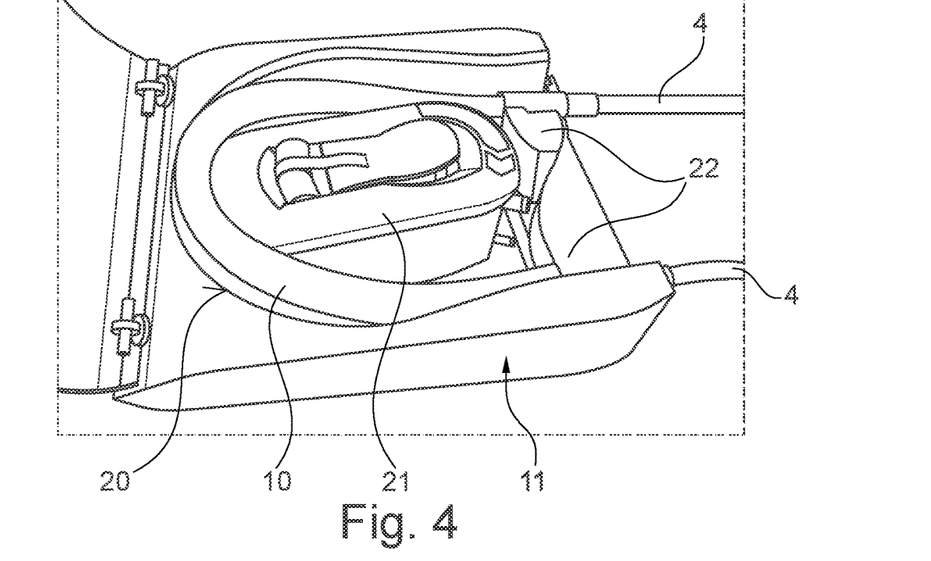
FIG. 4 shows a detailed view of a blood pump of the apparatus during preparation.

FIG. 4 illustrates a detailed view of a blood pump 10 of the apparatus during preparation. The pump segment 10 is inserted in the retaining contour 22 but is not yet occluded between the rotor 21 and the guiding surface 20. In order to be capable of displacing air contained in the blood system in a preferably residue-free and complete manner, the arterial blood line 4 and the pump segment 10 in this case are advantageously filled from the bottom to the top, which is why the blood pump 11 is arranged and oriented at the apparatus so that it is opened towards the side (cf. also FIGS. 1, 2 and 3).

Figure 5:
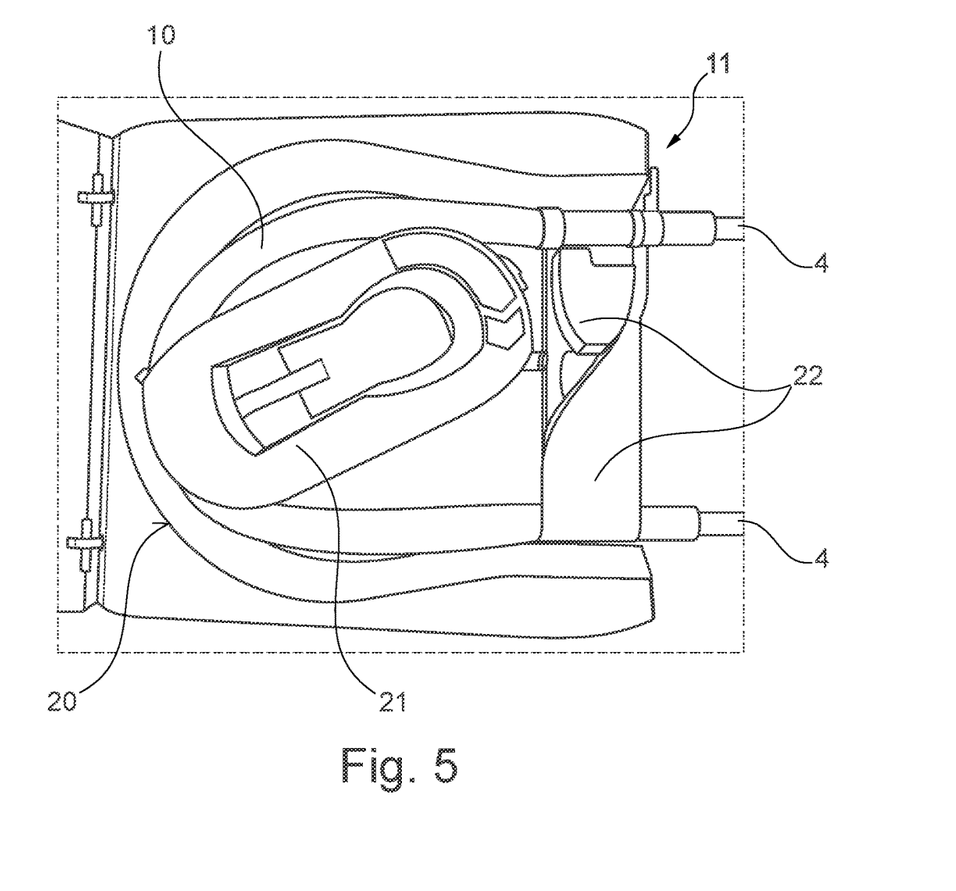
FIG. 5 shows a detailed view of the blood pump of the apparatus during blood treatment.

FIG. 5 illustrates a detailed view of the blood pump 11 of the apparatus during blood treatment after the first sequence of priming, viz. after complete filling of the blood system with priming liquid. The pump rotor 21 has been rotated out of the position as shown in FIG. 4 and the pump segment 10 has been automatically caught by the rotor 21 and threaded between the latter and the guiding surface 20. At least one roll of the rotor 21 then is engaged with the pump segment 11 and occludes the same. As soon as the pump segment 10 has been threaded, the blood pump 11 can be used for delivery. The priming liquid contained in the blood system can be circulated within the latter until a patient is connected and treatment is started.

The invention claimed is:

1. A method of priming an extracorporeal blood system, the extracorporeal blood system comprising an arterial blood line, a venous blood line, a pump segment for interaction with a blood pump of the apparatus, and a blood treatment unit, the method comprising the steps of:
   connecting a port of the venous blood line to a venous blood port of the blood treatment unit;
   connecting a port of the arterial blood line to an arterial blood port of the blood treatment unit;
   connecting the extracorporeal blood system to a reservoir containing priming liquid; and
   filling the extracorporeal blood system with priming liquid,
   the pump segment being inserted into or positioned relative to the blood pump prior to filling with priming liquid so that during filling of priming liquid into the extracorporeal blood system, the pump segment is not occluded by the blood pump and, after complete filling of the extracorporeal blood system with priming liquid, the pump segment is automatically placed and occluded in the delivery path of the blood pump by activating the blood pump.

2. The method according to claim 1, wherein the extracorporeal blood system is connected to the reservoir containing priming liquid, as a patient-side port of the venous blood line or a patient-side port of the arterial blood line or a filling line being fluid-connected thereto is connected to the reservoir containing priming liquid.

3. The method according to claim 2, wherein the patient-side port of the venous blood line is connected to the reservoir containing priming liquid and subsequently the extracorporeal blood system is filled from the arterial side to the venous side with priming liquid, wherein the reservoir is a substitute port of the apparatus or an external container containing priming liquid, or in that the patient-side port of the arterial blood line is connected to the reservoir containing priming liquid and subsequently the extracorporeal blood system is filled from the venous side to the arterial side with priming liquid, wherein the reservoir is the substitute port of the apparatus or the external container containing priming liquid.

4. The method according to claim 1, wherein, prior to filling with priming liquid, a patient-side port of the venous blood line or a patient-side port of the arterial blood line is connected to a process liquid port of the apparatus for extracorporeal blood treatment or to a separate process liquid reservoir.

5. The method according to claim 1, wherein during priming after filling with priming liquid, the blood pump is operated in a delivery direction which is opposed to the delivery direction during blood treatment.

6. The method according to claim 1, wherein, prior to filling with priming liquid, the blood system is connected to the apparatus for extracorporeal blood treatment in a manner intended for treatment, with the exception that the pump segment is not occluded.

7. The method according to claim 1, wherein, prior to filling of the extracorporeal blood system with priming liquid, a sensor test run is carried out by closing the arterial blood line and/or the venous blood line and pressure is increased in the extracorporeal blood system.

8. The method according to claim 1, wherein the priming liquid is filled into the extracorporeal blood system by excess pressure on a substitute port of the apparatus or hydrostatic pressure.

* * * * *